(12) United States Patent
Golovanevsky

(10) Patent No.: US 9,970,886 B2
(45) Date of Patent: May 15, 2018

(54) METROLOGY TOOL STAGE CONFIGURATIONS AND OPERATION METHODS

(71) Applicant: KLA-Tencor Corporation, Milpitas, CA (US)

(72) Inventor: Boris Golovanevsky, Haifa (IL)

( * ) Notice: Subject to any disclaimer, the term of this patent is extended or adjusted under 35 U.S.C. 154(b) by 0 days. days.

(21) Appl. No.: 14/569,043

(22) Filed: Dec. 12, 2014

(65) Prior Publication Data

US 2015/0098081 A1    Apr. 9, 2015

Related U.S. Application Data

(63) Continuation of application No. PCT/US2014/046213, filed on Jul. 10, 2014.

(60) Provisional application No. 61/845,358, filed on Jul. 11, 2013, provisional application No. 61/865,611, filed on Aug. 14, 2013, provisional application No. 61/866,015, filed on Aug. 14, 2013.

(51) Int. Cl.
*G01N 21/00* (2006.01)
*G01N 21/95* (2006.01)
*H01L 21/687* (2006.01)

(52) U.S. Cl.
CPC ... *G01N 21/9501* (2013.01); *H01L 21/68764* (2013.01); *G01N 2201/02* (2013.01); *Y10T 29/49* (2015.01)

(58) Field of Classification Search
CPC ......... G01N 21/00; G03B 21/00; G02B 15/00
USPC ............................ 356/237.2–237.6, 601–614
See application file for complete search history.

(56) References Cited

U.S. PATENT DOCUMENTS

| | | | |
|---|---|---|---|
| 4,573,791 A * | 3/1986 | Phillips | G03F 9/70 355/43 |
| 5,105,147 A * | 4/1992 | Karasikov | G01R 31/2656 324/537 |
| 6,157,450 A * | 12/2000 | Marchese-Ragona | G01B 11/306 356/237.1 |
| 6,224,670 B1 * | 5/2001 | Ishida | H01L 21/67028 118/429 |

(Continued)

FOREIGN PATENT DOCUMENTS

JP      04-112551 A    4/1992
JP      11-121577 A    4/1999

(Continued)

*Primary Examiner* — Isiaka Akanbi
(74) *Attorney, Agent, or Firm* — Suiter Swantz pc llo

(57) ABSTRACT

Metrology tool stage configurations and respective methods are provided, which comprise a pivoted connection arranged to receive a wafer and enable rotation thereof about a pivot; a radial axis arranged to radially move the rotatable pivoted connection attached thereto; and optics having a stationary part configured to generate a collimated illumination beam. For example, the optics may be stationary and the radial axis may be centrally rotated to enable stage operation without requiring additional space for guiding systems. In another example, a part of the optics may be rotatable, when configured to receive illumination via a mechanically decoupled or empty region, receive power and control wirelessly and deliver data wirelessly. The disclosed configurations provide more compact and more robust stages which efficiently handle large wafers. Stage configurations may be horizontal or vertical, the latter further minimizing the tool's footprint.

37 Claims, 8 Drawing Sheets

(56) References Cited

U.S. PATENT DOCUMENTS

| | | | | |
|---|---|---|---|---|
| 6,263,099 B1* | 7/2001 | Maeda | ............... | G01N 21/8806 |
| | | | | 356/394 |
| 6,320,609 B1* | 11/2001 | Buchanan | ................ | G02B 7/00 |
| | | | | 348/126 |
| 7,295,314 B1 | 11/2007 | Spady et al. | | |
| 7,619,752 B2* | 11/2009 | Liphardt | .............. | G01N 21/211 |
| | | | | 356/620 |
| 2002/0150456 A1* | 10/2002 | Kim | ........................ | B25J 18/02 |
| | | | | 414/728 |
| 2003/0016338 A1* | 1/2003 | Yasuda | .................. | G03B 27/52 |
| | | | | 355/55 |
| 2003/0159528 A1* | 8/2003 | Kim | .................. | G01N 21/9501 |
| | | | | 73/865.8 |
| 2007/0115457 A1* | 5/2007 | Matsuzawa | ........ | G01M 11/0264 |
| | | | | 356/124 |

FOREIGN PATENT DOCUMENTS

| | | |
|---|---|---|
| JP | 2002-043393 A | 2/2002 |
| JP | 2009-031125 A | 2/2009 |

\* cited by examiner

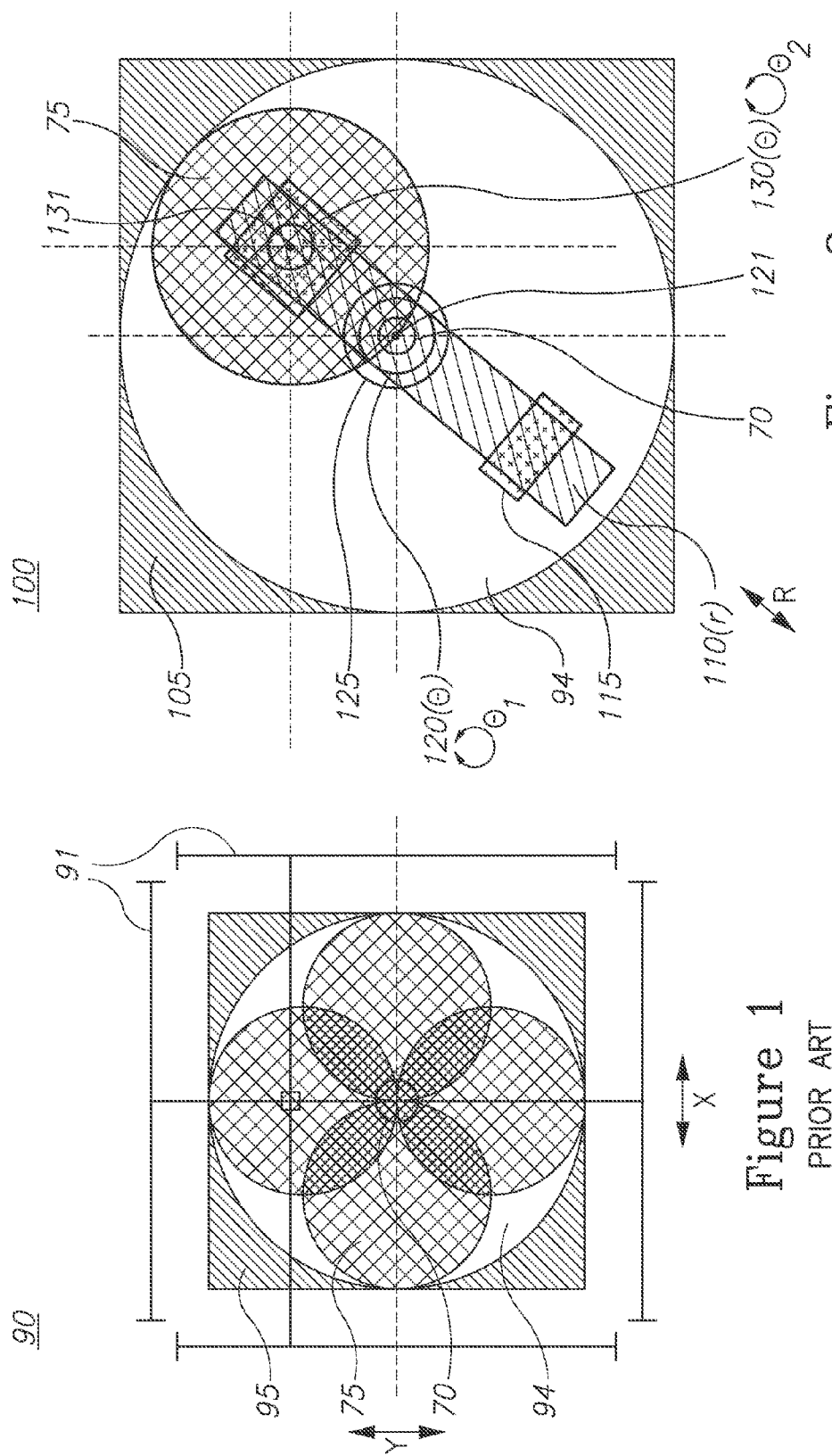

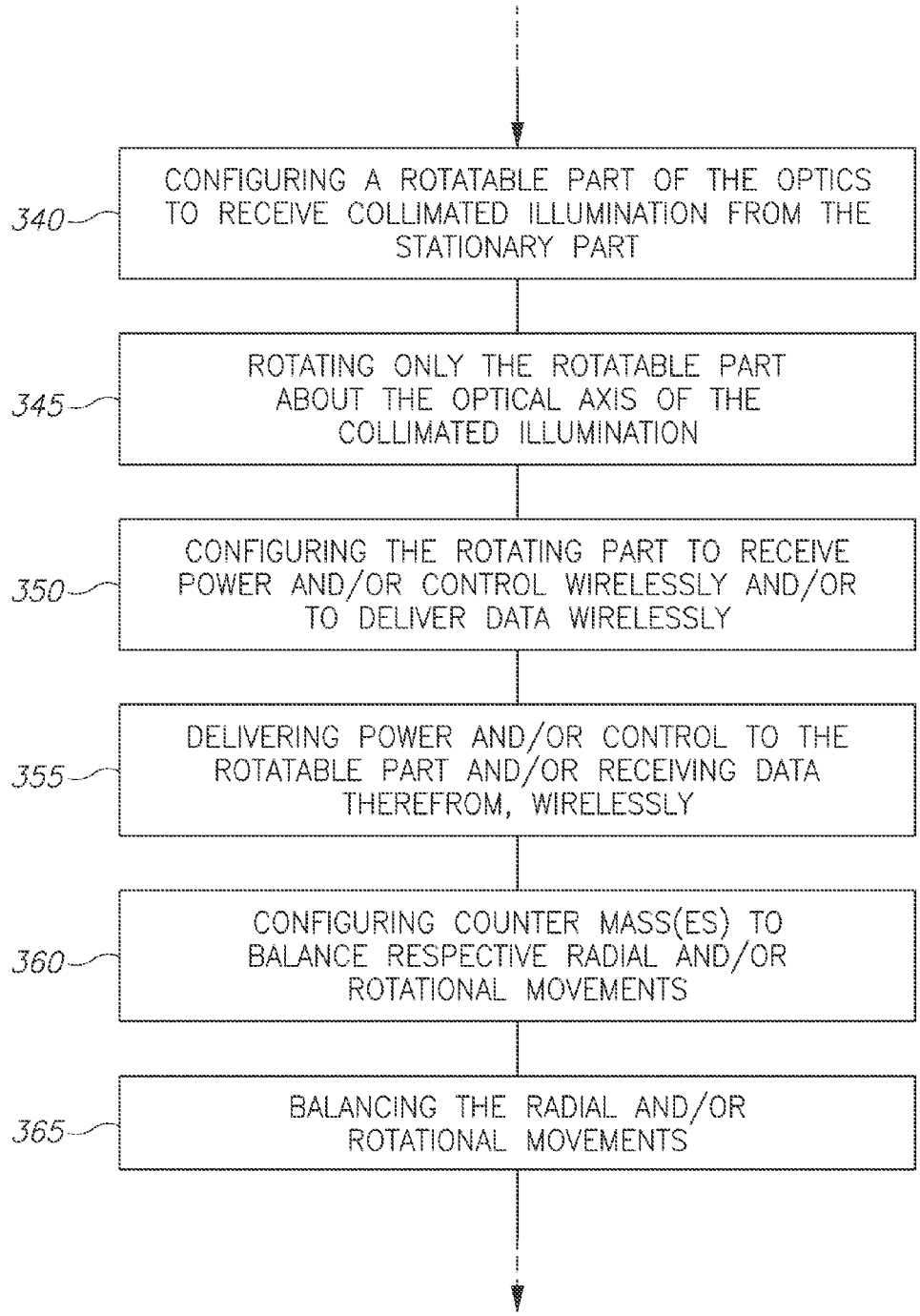
Figure 6 (cont. 1)

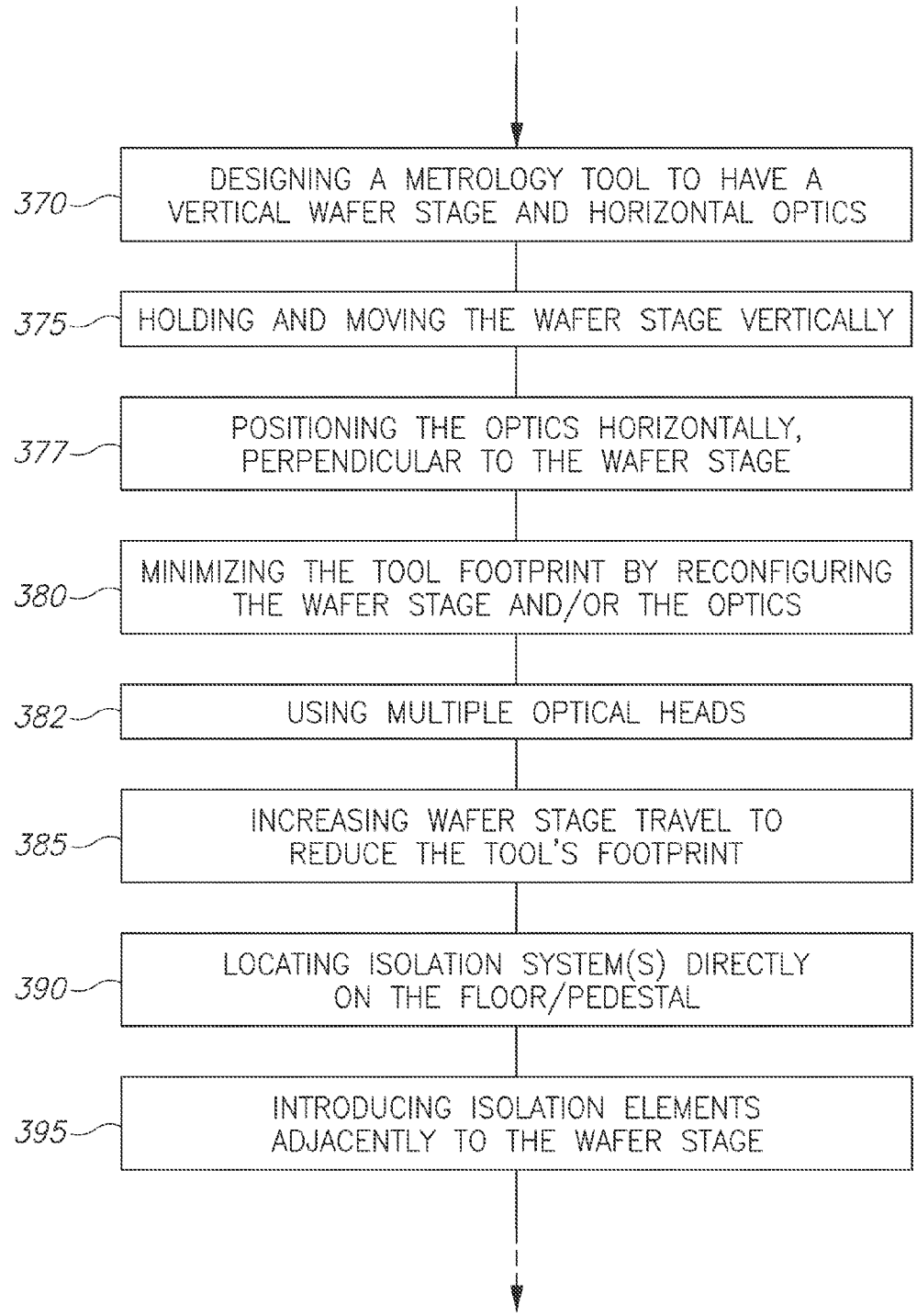
Figure 6 (cont. 2)

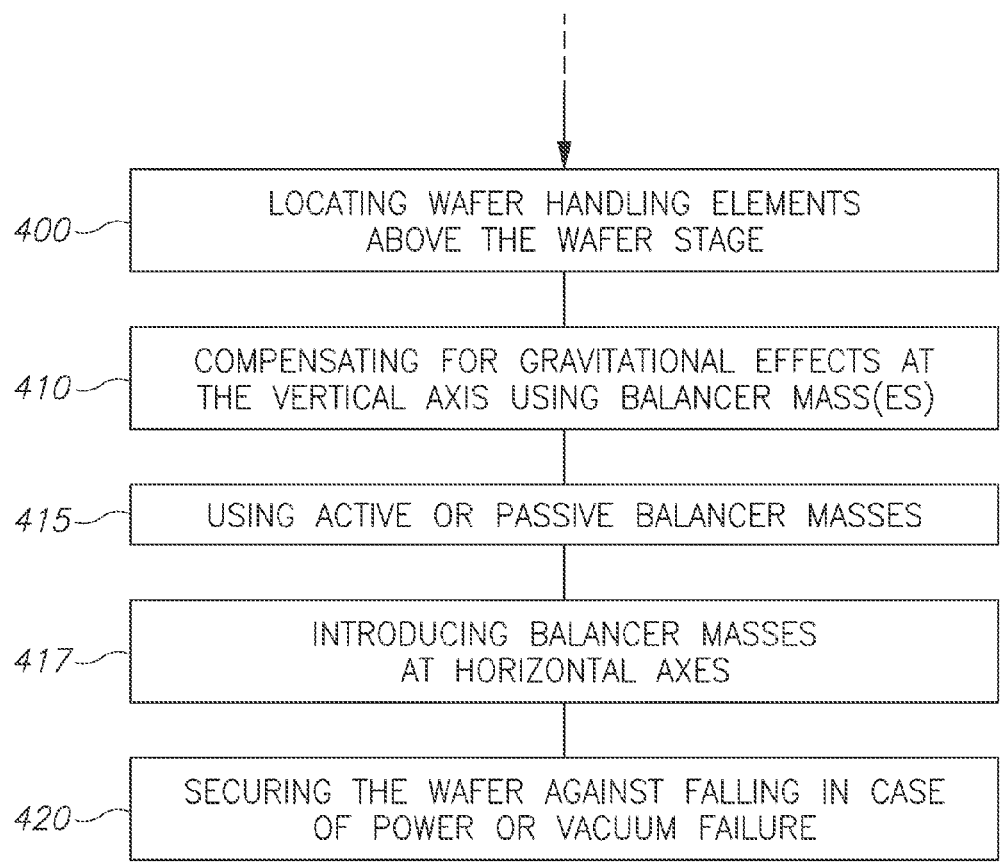
Figure 6 (cont. 3)

METROLOGY TOOL STAGE CONFIGURATIONS AND OPERATION METHODS

CROSS REFERENCE TO RELATED APPLICATIONS

This application is filed under 35 U.S.C. § 111(a) and § 365(c) as a continuation of International Patent Application No. PCT/US14/46213, filed on Jul. 10, 2014, which application claims the benefit of U.S. Provisional Patent Application No. 61/845,358, filed on Jul. 11, 2013, and of U.S. Provisional Patent Application Nos. 61/865,611 and 61/866,015, both filed on Aug. 14, 2013, which applications are incorporated herein by reference in their entireties.

BACKGROUND OF THE INVENTION

1. Technical Field

The present invention generally relates to the field of metrology tools, and, more particularly, to metrology tool stage design.

2. Discussion of Related Art

Metrology tool stages allow respective positioning of wafers and optics to enable measurement of wafer areas. Typical metrology tool stage configurations suffer from different limitations such as leaving a large tool footprint, ineffectively using the stage travel, and are limited in the stage acceleration due to large moving masses and stack of the axes. These configurations have other limitations in stage stiffness due to large axis strokes, in stage flatness at wafer level, and in counter-mass implementation, thus most of the stage impact is transferred directly to the environment. As wafers increase in size, these problems are increased and compounded.

FIG. 1 is a high level schematic illustration of a metrology tool stage configuration 90 according to the prior art. In the prior art, movements of wafer 75 are conducted in two linear and perpendicular directions, denoted in FIG. 1 by X and Y. Wafer 75 is moved into a position in which the measured wafer area is under the central and stationary optics 70. Wafer movements X, Y are controlled by a guiding system 91 comprising external movement guides and attachment means to wafer 75. A footprint 94 is the area required to accommodate all possible wafer movements (wafer travel). It is noted that in the prior art, the stage system uses beyond footprint 94 also a circumference of footprint 94 which occupies guiding system 91. Furthermore, the immediate vicinity of footprint 94, which includes areas 95 of the square bounding footprint 94 and having sides with the diameter of footprint 94, likewise cannot be used for any purposes (e.g., supporting optics 70) in order not to obstruct the operation and free movement of guiding system 91, and is hence a wasted stage space.

As wafer sizes increase, stage travel and moving mass increase dramatically and together, with demanded increase in acceleration, require unrealistically high power motors which generate a lot of heat and again increase the moving mass. Short move and settle time require extremely high mechanical stiffness of stage axes, which again leads to increasing the moving mass. These considerations are not conducive to providing a small tool foot print. The typical approach of orthogonal XY stage is very inefficient in term of wafer coverage to stage foot print ratio, as shown in FIG. 1.

It is noted that typical configurations with stationary optics are configured to move along perpendicular axes X, Y and not along radial and rotation axis, while typical configurations with rotatable wafers also have rotatable and/or linearly movable optics. The former has the disadvantage of a relatively large footprint and unused footprint periphery (occupied by guiding systems and left free to enable guiding system operation), while the latter is complex and slow in the operation of the moving optics and suffers inaccuracies due to the movements of the optics.

Therefore, there is a long-felt need for an improved metrology tool stage configuration that allows a small footprint associated with a tool, and fast in the operation of the moving optics without sacrificing accuracy.

SUMMARY OF THE INVENTION

The present invention provides a metrology tool stage configuration, comprising a pivoted connection operatively arranged to receive a wafer and enable rotational movement thereof about a pivot, a radial axis operatively arranged to move radially and enable radial movement, the rotatable pivot connection attached thereto, and optics having a stationary part configured to generate a collimated illumination beam.

The present invention also provides a method, comprising the steps of designing a metrology tool to have a vertical wafer stage and horizontal optics, holding and moving the wafer stage vertically, and positioning the optics perpendicularly to the wafer stage to minimize a footprint associated with a tool.

The present invention also provides a method, comprising the step of carrying out metrology measurements with optics, moving a wafer radially while carrying out metrology measurements, moving a wafer rotationally, and, maintaining at least a part of the optics stationary.

The present invention also provides a computer program product, comprising a computer readable storage medium having a computer readable program embodied therewith, wherein the computer readable program is configured to control radial and rotational movements of a wafer, while at least a part of accompanying optics are kept stationary.

The present invention further provides a metrology tool, comprising a metrology tool stage configuration, comprising a pivoted connection arranged to receive a wafer and enable rotation thereof about a pivot, a radial axis arranged to move radially the rotatable pivot connection attached thereto, and, optics having a stationary part configured to generate a collimated illumination beam and a computer program product comprising a computer readable storage medium having computer readable program embodied therewith, the computer readable program configured to control radial and rotational movements of a wafer, while at least a part of respective optics are kept stationary, wherein the computer program product is configured to control the metrology tool stage.

A metrology tool, comprising a metrology tool stage configuration comprising a vertical wafer stage, and, optics perpendicular thereto, and, a computer program product comprising a computer readable storage medium having computer readable program embodied therewith, the computer readable program configured to control radial and rotational movements of a wafer, while at least a part of respective optics are kept stationary, wherein the computer program product is configured to control the metrology tool stage.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 1 is a high level schematic illustration of a metrology tool stage configuration according to the prior art;

FIG. 2 is a high level schematic illustration of a metrology tool stage configuration, according to some embodiments of the invention;

DETAILED DESCRIPTION OF THE INVENTION

Figure 3:
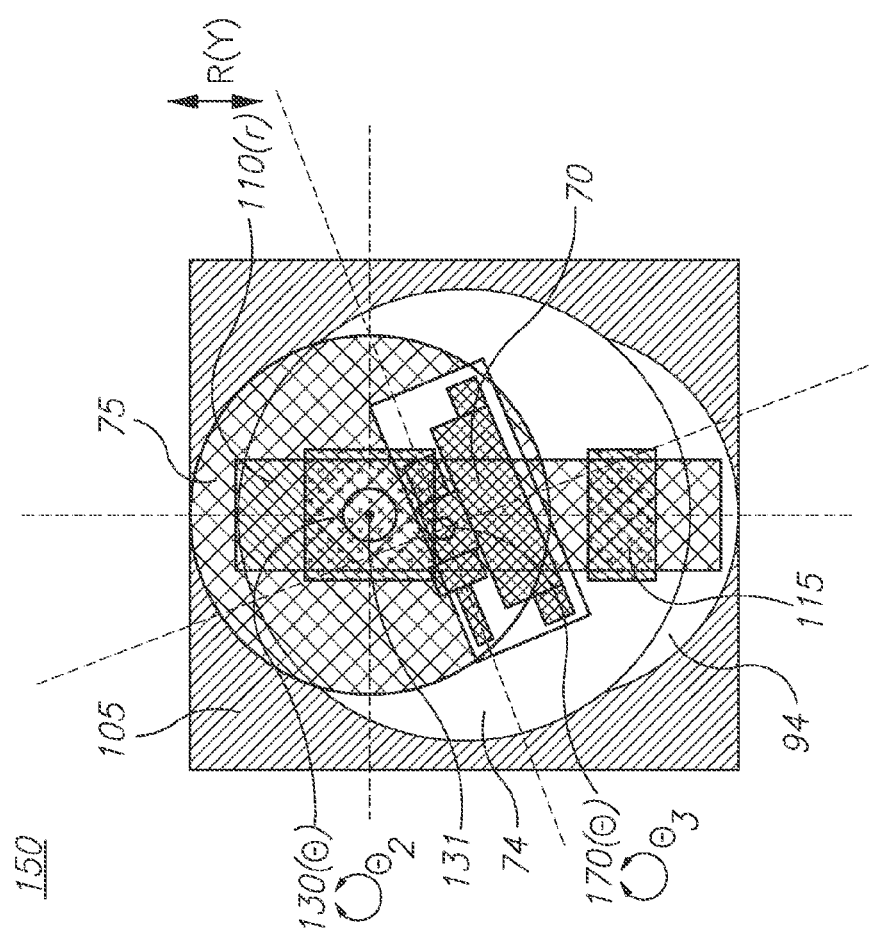
FIG. 3 is a high level schematic illustration of a metrology tool stage configuration, according to some embodiments of the invention.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Metrology tool stage configurations and respective methods are provided, which comprise a pivoted connection arranged to receive a wafer and enable rotation thereof about a pivot; a radial axis arranged to move radially the rotatable pivot connection attached thereto; and optics having a stationary part configured to generate a collimated illumination beam. For example, the optics may be stationary and the radial axis may be centrally rotated to enable stage operation without requiring additional space for guiding systems. In another example, a part of the optics may be rotatable, when configured to receive illumination via a mechanical decoupled or empty region, receive power and control wirelessly and deliver data wirelessly. The disclosed configurations provide more compact and more robust stages which efficiently handle large wafers. Stage configurations may be horizontal or vertical, with the latter further minimizing the tool's footprint.

The disclosed invention comprises tool stage configurations and implementations that enhance throughput performance and reduce the tool footprint. Disclosed solutions utilize less space around the footprint defined by wafer movements and hence provide more compact stages and thus more compact tools. Disclosed solutions reduce vibrations within the system as well as vibration delivered to the environment by the compactness as well as by better arrangement of moving elements and counter-masses.

Figure 4:
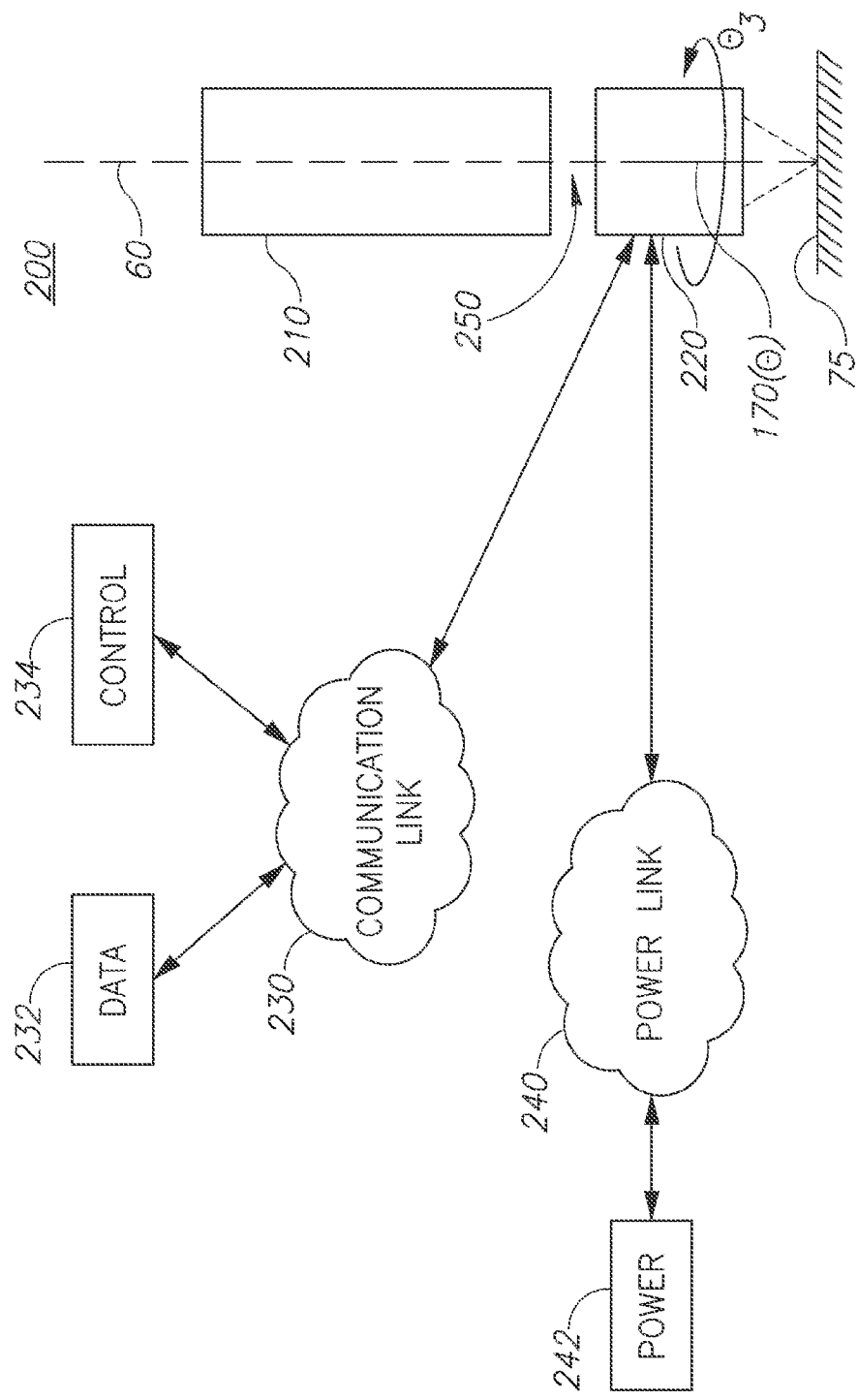
FIG. 4 is a high level schematic illustration of optics, according to some embodiments of the invention.

Disclosed are metrology tool stage configurations 100 (shown in FIG. 2) and 150 (shown in FIG. 3) comprising (i) pivoted connection 130 arranged to receive wafer 75 and enable rotation thereof (θ, denoted by arrow $\theta_2$) about pivot 131; radial axis 110 arranged to move radially (r) with rotatable pivot connection 130 attached thereto (FIGS. 2 and 3); and optics 70 having a stationary part configured to generate a collimated illumination beam (see FIG. 4).

FIG. 2 is a high level schematic illustration of a metrology tool stage configuration 100, according to some embodiments of the invention. In configuration 100, the optics is central and stationary, and all movements are carried out by wafer 75. Configuration 100 further comprises central pivoted connection 120 arranged to receive radial axis 110 and enable rotation thereof (θ, denoted by arrow $\theta_1$) about central pivot 121. The combination of radial movement R and rotational movements $\theta_1, \theta_2$ enable moving wafer 75 throughout footprint 94 defined by radial axis 110 and central pivoted connection 120 (similar in its extent to footprint 94 illustrated in FIG. 1 for same sized wafers 75). However, in contrast to prior art configurations 90, configurations 100 dispose of guiding system 91 and may utilize the evacuated space for other purposes. Moreover, area 105 between the square bounding footprint 94 (which is the stage footprint) and footprint 94 itself (which is the wafer travel footprint) may be used without hindering the operation of the tool stage (in contrast to respective prior art area 95 which could not be used without hindering the wafer movements along the X and Y axes, see FIG. 1). For example optics 70 may be supported (at least partially) within area 105 and hence enable constructing more compact stages.

It is noted that the required change in axial movement R is merely half the required movements X, Y in prior art configurations 90, due to the introduction of central rotation $\theta_1$. Furthermore, the added degree of freedom ($\theta_1$) enables using azimuth sensitive motion algorithms that reduced the travel time and extent, and thus increase wafer throughput through the tool. Certain embodiments of the invention comprise such algorithms as well as algorithms for efficient conversion of X, Y coordinates to R, $\theta_1$, $\theta_2$ coordinates.

Any of movements R and $\theta_1$ (possibly also $\theta_2$) may be balanced by respective counter masses 115, 125 to reduce vibrations and enhance the accuracy of the system.

FIG. 3 is a high level schematic illustration of metrology tool stage configuration 150, according to some embodiments of the invention. Configurations 150 combine rotations of a part of central optics 200 (FIG. 4), which are complemented by movements of wafer 75 (using an RO stage with stationary radial axis 110). FIG. 4 is a high level schematic illustration of optics 200, according to some embodiments of the invention.

Optics 200 may comprise rotatable part 220 arranged to receive collimated illumination from stationary part 210 along optical axis 60. The collimated illumination may be delivered from stationary part 210 to rotatable part 220 via gap 250 (e.g., air, vacuum or filled with other media) that mechanically decouples parts 210, 220. Rotatable part 220 is configured to be rotatable ($\theta_3$) about optical axis 60, e.g., about rotation axis 170, and cover footprint 74, which may be designed according to specified requirements (e.g., may have a larger radius or a smaller radius than wafer 75). In certain embodiments, rotatable part 210 may be configured to receive power 242 and control 234 and to deliver data 232 wirelessly, e.g., via respective power link(s) 240 and communication link(s) 230. In certain embodiments, transfer of power 242, data 232 and control 234 may be implemented using known protocols. Alternatively or complementary, transfer of any of power 242, data 232 and control 234 may be carried out mechanically, e.g., via multiple-passage rotary unions.

Configuration 150 thus uses smaller footprint 94 than configuration 100 (as radial axis 110 is not rotated) and leaves area 105 free for utilization. While optics 200 has to be partially rotated to enable all required wafer positions within smaller footprint 94, rotation is limited to small part 220 of optics to minimize vibrations and inaccuracies arising in prior art configurations which require rotating and/or moving the whole optics system.

Configuration 150 may further enable using multiple measurement heads as rotatable part 220 without increasing the footprint and possibly enable easy head replacements. Configuration 150 may further comprise using simple linear stage and/or slider to move the optics between predefined discrete positions and/or using simple sensors for accurate optical head positioning at predefined discrete locations.

Movements R (possibly also $\theta_2$, $\theta_3$) may be balanced by respective counter masses 115 to reduce vibrations and enhance the accuracy of the system. Any of radial axis 110, central pivoted connection 120, pivoted connection 130, and rotation axis 170 may be implemented using air bearings to improve the stage stiffness, flatness, accuracy and repeatability. Magnetic levitation technology may also be used instead of or in combination with air bearings. Hybrid approaches may also be implemented. Such arrangements may be utilized to increase stiffness, increase flatness and straightness, eliminate the tolerances buildups from stacked axes and improve stage accuracy, resolution and repeatability.

The disclosed invention uses radial-rotational configuration to maintain the large footprint, but to free the periphery of the footprint for use and/or configure the optics to rotate only in small part to avoid the complexity and inaccuracies involved in moving the whole optics.

Figure 5B:
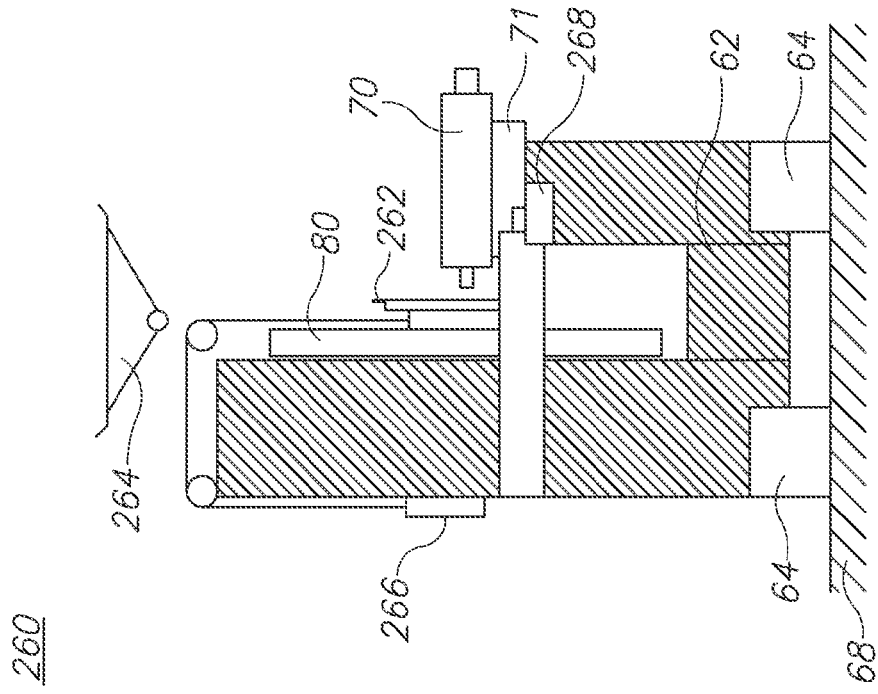
FIG. 5B is a high level schematic illustrations of a vertical metrology tool stage configuration, according to some embodiments of the invention; and, FIG. 6 is a high level flowchart illustrating a method, according to some embodiments of the invention.
Figure 5A:
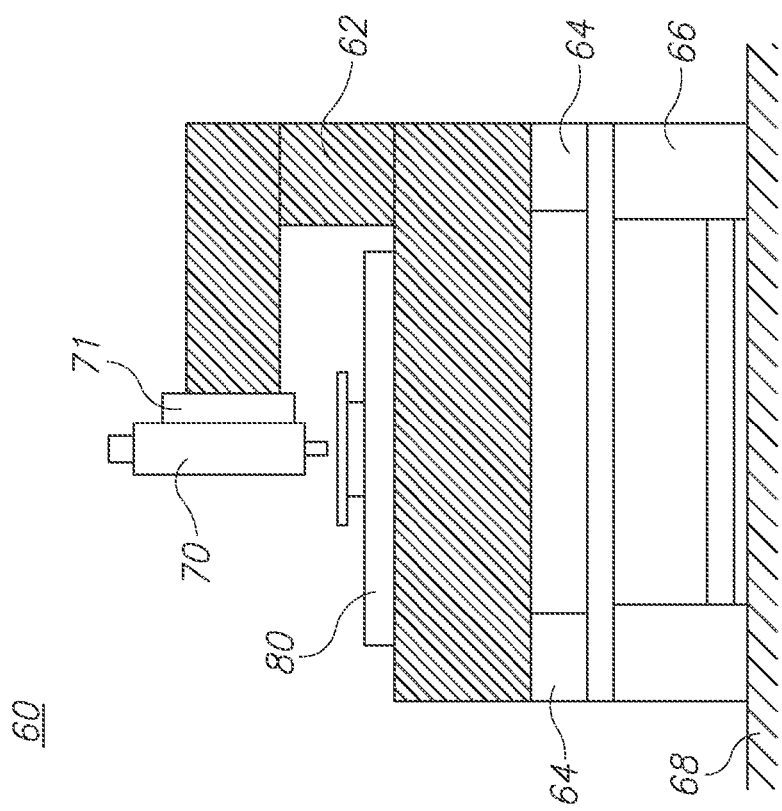
FIG. 5A is a high level schematic illustration of a horizontal metrology tool stage configuration, according to some embodiments of the invention.

FIGS. 5A and 5B are high level schematic illustrations of horizontal and vertical metrology tool stage configurations, respectively, according to some embodiments of the invention. FIG. 5A schematically illustrates configuration 60 with horizontal wafer stage 80. Configuration 60 may utilize typical XY wafer stages 90, typical Rθ wafer stages with movable optics, or any of configurations 100, 150 disclosed in the current invention, exhibiting angular motion 120 of radial axis 110 and/or optics configuration 200 with a main stationary optics part 210 and smaller rotatable part 220, coupled optically and wirelessly to stationary part 210.

FIG. 5B is a schematic illustration of tool configuration 260 having vertical wafer stage 80. Vertical wafer stage 80 may be configured as any of the stage configurations listed above, including both typical XY and RO stage configurations 90 and 150 with movable optics, as well as embodiments of the disclosed invention with at least partly stationary optics such as configuration 100 with rotatable radial axis 110 or configuration 150 with partly stationary optics 200. Further, wafer stage 80 may be adapted to its vertical position.

Tool configurations 60, 260 comprise Z stage 71, moving optics 70 vertically in configuration 60 and moving optics 70 horizontally in configuration 260; tool body 62, made e.g., of granite and comprising e.g., an optics bridge; isolation system 64 for reducing vibration transfer between the respective tool and the environment, as well as bench 66 and a floor or pedestal 68.

In configuration 260, wafer stage 80 is rotated to a vertical position and optics 70 is respectively positioned horizontally. Advantageously, the vertical orientation of wafer stage 80 reduces the space occupied by the metrology tool and increases the tool's throughput. Particularly as wafers become larger, the advantages of the disclosed approach are enhanced. In combination with the stage and optics configurations 100, 150, 200 disclosed above, the tool's footprint may be maintained acceptable even when handling larger wafers. Furthermore, the vertical stage position enables more efficient handling of stage travel and shortens movement and settling durations.

In certain embodiments, configuration 260 further comprises chuck 262 supporting wafer stage 80 with integrated security means for securing the wafer against falling in case of power or vacuum failure. Chuck 262, such as a vacuum chuck, may comprise an integrated edge grip mechanism configured to secure the wafer and prevent the wafer from falling down in case a power or vacuum shutdown occurs. The edge grip may be "normally closed" and open only when the chuck vacuum and power are on. Chuck 262 may be configured to enable leveling the Z stage to eliminate a coarse stroke requirement vertically to the stage.

In certain embodiments, configuration 260 further comprises component(s) 268 of isolation system in close proximity to vertical wafer stage 80. For example, components 268 may comprise linear motors that balance and isolate vertical movements and vibrations. Components 268 may be considered remote elements of distributed isolation system 64. Components 268 may be configured to compensate of relative movements of chuck 262 and wafer stage 80 with respect to optics 70, e.g., using feeds from wafer stage 80 and/or floor 68. In certain embodiments, isolation system 64 may be located directly on floor or pedestal 68 with the corresponding leveling mechanism.

In certain embodiments, configuration 260 further comprises a wafer flipping and pre-aligning mechanism 264 configured to handle the wafers with respect to vertical wafer stage 80. Wafer handling mechanism 264 may be located directly above optics 70 at the level of standard robot load/unload reach.

In certain embodiments, configuration 260 further comprises a vertical axis balancer mass mechanism 266 configured to cancel gravitational effects of re-positioning wafer stage 80 vertically. Balancer mass 266 is configured to cancel or reduce vibrations caused by the vertical movement of wafer stage 80. In certain embodiments, configuration 260 further comprises horizontal balancer masses to damp horizontal vibrations as well.

Advantageously, turning wafer stage 80 vertically changes the footprint and vibration limitation on the tool as different dimensions count as limiting the footprint and determining the interaction with the environment. For example, only one dimension (formerly horizontal) of wafer stage 80 affects the footprint as compared with two (horizontal) dimensions in the horizontal configuration. The vertical dimension of wafer stage 80 is compounded with the dimensions of the optics to affect the tool's footprint in the vertical configuration. Optics 70 or 200 may be configured to reduce the horizontal dimension, e.g., by folding the optical axes to reduce the footprint. In case of multiple optical heads, the stage travel may be increased in the direction which reduces the footprint impact.

Figure 6:
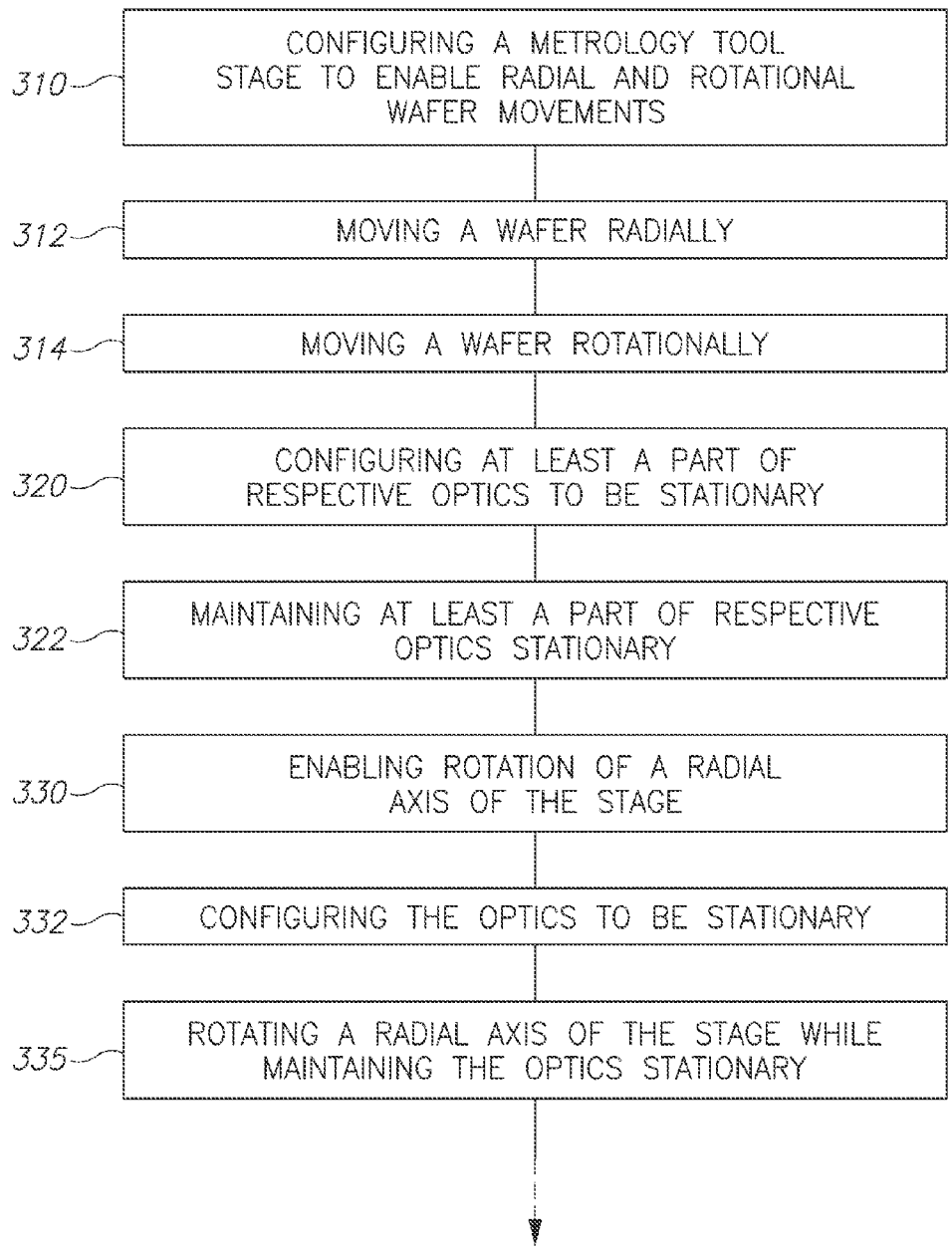

FIG. 6 is a high level flowchart illustrating a method 300, according to some embodiments of the invention. Method 300 comprises configuring a metrology tool stage to enable radial and rotational wafer movements (stage 310) and configuring at least a part of respective optics to be stationary (stage 320).

In certain embodiments, method 300 further comprises enabling rotation of a radial axis of the stage (stage 330) and configuring the optics to be stationary (stage 332).

In certain embodiments, method 300 further comprises configuring a part of the optics to receive collimated illumination from the stationary part (stage 340) and to be rotatable about an optical axis of the collimated illumination. Method 300 may further comprise configuring the rotatable part to receive power and control and to deliver data wirelessly (stage 350).

Method 300 may, in any of the embodiments, further comprise configuring at least one counter mass to balance respective at least one of the radial and rotational movements (stage 360).

Method 300 may further comprise stages of operating stage tool configurations 100, 150 and optics 200. Method 300 may comprise carrying out metrology measurements by moving a wafer radially (stage 312) and rotationally (stage 314) while maintaining at least a part of respective optics stationary (stage 322).

Method 300 may comprise rotating a radial axis of the stage while maintaining the optics stationary (stage 335).

Method 300 may comprise rotating only a part of the optics that receives collimated illumination from the stationary part, about an optical axis of the collimated illumination (stage 345). Method 300 may further comprise delivering power and/or control to the rotatable part and/or receiving data therefrom, wirelessly (stage 355).

Method 300 may, in any of the embodiments, further comprise balancing at least one of the radial and rotational movements (stage 365), e.g., using counter-masses.

Advantageously, disclosed configurations 100, 150 may achieve the minimum tool footprint for required stage travel; eliminate the tolerances buildups from stacked linear axis (see FIG. 1); improve the stage dynamics and reduce the move and settle time by reducing the moving masses, lowering the stage profile/stack, increasing stiffness and shortening the axis stroke; and improve the total stage flatness at chuck level especially when air bearing is used. In certain embodiments, configurations 100, 150 may be designed to eliminate the tolerances' buildups from stacked linear axes and to improve the total stage flatness at chuck leveling (especially when air bearings are used). In certain embodiments, the improved stage movements and configurations may be used to reduce the coarse Z stroke or even eliminate it, leaving the Z range to be fully covered by fine Z axis only. Method 300 may further comprise leveling the stage to eliminate a coarse stroke requirement vertically to the stage.

Method 300 may further comprise configuring the tool stage to move a wafer attached thereto horizontally and move the optics perpendicularly to the wafer; or configuring the tool stage to move a wafer attached thereto vertically and to move the optics perpendicularly to the wafer. Any of the above stages may be adapted to either vertical or horizontal configuration of the wafer stage, and corresponding perpendicular configuration of the optics.

Method 300 may further comprise designing a metrology tool to have a vertical wafer stage and horizontal optics (stage 370), holding and moving the wafer stage vertically (stage 375) and positioning the optics horizontally, perpendicular to the wafer stage (stage 377), to minimize the tool footprint by the reconfiguring of the wafer stage and/or the optics (stage 380).

In certain embodiments, method 300 may further comprise using multiple optical heads (stage 382).

In certain embodiments, method 300 may further comprise increasing wafer stage travel to reduce the tool's footprint (stage 385).

In certain embodiments, method 300 may further comprise locating isolation system(s) directly on the floor/pedestal (stage 390) and/or introducing isolation elements adjacently to the wafer stage (stage 395).

Method 300 may further comprise locating wafer handling elements above the wafer stage (stage 400) and/or compensating for gravitational effects at the vertical axis using balancer mass(es) (stage 410).

Method 300 may further comprise using active or passive balancer masses (stage 415) and/or introducing balancer masses at horizontal axes (stage 417).

Method 300 may further comprise securing the wafer against falling in case of power or vacuum failure (stage 420).

Certain embodiments comprise a computer program product comprising a computer readable storage medium having computer readable program embodied therewith, the computer readable program configured to control radial and rotational movements of a wafer, while at least a part of respective optics is kept stationary. The computer readable program may further comprise computer readable program configured to control rotation of a radial axis of the wafer, while maintaining the optics stationary. The computer readable program may further comprise computer readable program configured to control rotation of a part of the optics that receives collimated illumination from the stationary part, about an optical axis of the collimated illumination. The computer readable program may further comprise computer readable program configured to control the rotatable part, power delivery thereto and data retrieval therefrom. The computer readable program may further comprise computer readable program configured to control movements of at least one counter mass to balance at least one of the radial and the rotational movements. The computer readable program may further comprise computer readable program configured to control horizontal wafer movements and vertical optics movements; or to control vertical wafer movements and horizontal optics movements, depending on the metrology tool configuration. The computer readable program may be further configured to control the operation of vertical or horizontal wafer stage and associated isolation system, balancing masses and wafer handling machinery.

Certain embodiments comprise a metrology tool comprising at least one of metrology tool stage configurations 100, 150 and a respective computer program product configured to control the metrology tool stage.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A metrology tool stage comprising:
   a pivoted connection arranged to receive a wafer and perform rotational movement of the wafer about a pivot substantially perpendicular to a planar surface of the wafer;
   a radial axis arranged to move radially and perform radial movement in a direction substantially parallel to the planar surface of the wafer, the pivoted connection attached thereto, wherein the metrology tool stage is configured as an R-Theta stage translated in accordance with an azimuth angle sensitive motion algorithm;
   wherein the metrology tool stage is configured with at least one counter mass configured to balance at least one of the radial and rotational movements; and
   a set of optics including a stationary part and a rotatable part, wherein the stationary part is configured to generate a collimated illumination beam and the rotatable part is configured to receive the collimated illumination beam from the stationary part, wherein the stationary part and the rotatable part are mechanically decoupled via a gap, wherein the rotatable part is positioned proximate to the wafer surface.

2. The metrology tool stage of claim 1, wherein the pivoted connection is centrally arranged to receive the radial axis and provide rotation of the radial axis about a central pivot.

3. The metrology tool stage of claim 2, wherein the set of optics are supported at least partially within a square area that bounds a footprint of the wafer, the area defined by the radial axis and the central pivoted connection.

4. The metrology tool stage of claim 1, wherein the rotatable part is configured to:
   receive power;
   receive control instructions; and
   wirelessly deliver data.

5. The metrology tool stage of claim 1, wherein the stage is leveled to eliminate a coarse stroke requirement vertically to the stage.

6. The metrology tool stage of claim 1, wherein the wafer is movable in a horizontal direction and the set of optics are arranged perpendicular to the wafer.

7. The metrology stage of claim 1, wherein the wafer is movable in a vertical direction and the set of optics are perpendicular to the wafer.

8. The metrology tool stage of claim 7, further comprising:
   a vertical wafer stage, wherein a line orthogonal to a receiving surface of the vertical wafer stage is substantially horizontal, wherein the set of optics are arranged perpendicular to the receiving surface of the vertical wafer stage; and
   optics perpendicular thereto.

9. The metrology tool stage of claim 8, further comprising:
   a chuck configured to support the vertical wafer stage; and
   a security means configured to secure the wafer.

10. The metrology tool stage of claim 8, further comprising:
    an isolation system, wherein the isolation system includes a first component located on at least one of a floor or a pedestal supporting the tool; and a second component proximate to the vertical wafer stage and configured to compensate for relative movements of the vertical wafer stage and the set of optics.

11. The metrology tool stage of claim 8, further comprising:
    a wafer handler configured to handle wafers with respect to the vertical wafer stage.

12. The metrology tool stage of claim 8, further comprising:
    a mass balancer configured to compensate for gravitational effects of re-positioning the wafer stage vertically.

13. The metrology tool stage of claim 8, the vertical wafer stage is leveled to eliminate a coarse stroke requirement vertically to the stage.

14. A method comprising:
    actuating, with a metrology tool stage, a wafer in a rotational direction about a pivot substantially perpendicular to a surface of the metrology tool stage;
    actuating, with the metrology tool stage, the wafer in a radial direction substantially parallel to the surface of the metrology tool stage, wherein movement of the metrology tool stage is in part determined by an azimuth angle sensitive motion algorithm, wherein the metrology tool stage includes a set of optics;
    securing at least a part of the set of optics of the metrology tool stage such that the at least a part of the set of optics are stationary relative to the surface of the metrology tool stage; and
    counter balancing the metrology tool stage, with at least one counter mass, at least one of radial or rotational movement.

15. The method of claim 14, further comprising:
    leveling the stage to eliminate a coarse stroke requirement vertically to the metrology tool stage.

16. The method of claim 14, further comprising:
horizontally actuating, with the metrology tool stage, the wafer; and
actuating, with the metrology tool stage, one or more parts of the set of optics perpendicularly to the wafer.

17. The method of claim 14, further comprising:
vertically actuating, with the metrology tool stage, the wafer; and
actuating, with the metrology tool stage, one or more parts of the set of optics perpendicularly to the wafer.

18. A method comprising:
providing a metrology tool having a vertical wafer stage and a set of optics arranged horizontally, wherein a line orthogonal to a receiving surface of the vertical wafer stage is substantially horizontal to the metrology tool, wherein the metrology tool is configured with at least one of active or passive balancer masses;
holding and moving the vertical wafer stage vertically;
positioning the set of optics perpendicularly to the vertical wafer stage to minimize a footprint associated with the metrology tool;
introducing, to the metrology tool, at least one of active or passive balancer masses; and
introducing, to the metrology tool, one or more balancer masses at a horizontal axis.

19. The method of claim 18, further comprising:
implementing multiple measurement heads; and
controlling wafer stage travel to reduce the footprint of the metrology tool.

20. The method of claim 18, further comprising:
positioning at least one isolation system component directly on a floor or pedestal supporting the tool; and
introducing isolation elements adjacent to the wafer stage.

21. The method of claim 18, further comprising:
positioning wafer handling elements above the wafer stage; and
compensating for gravitational effects using at least one balancer mass.

22. The method of claim 18, further comprising:
securing the wafer.

23. The method of claim 18, further comprising:
leveling the stage to eliminate a coarse stroke requirement vertically to the stage.

24. A method comprising:
performing one or more metrology measurements on a wafer disposed on an R-Theta stage with a set of optics;
performing an azimuth angle sensitive motion algorithm;
moving the wafer radially in a direction substantially parallel to a planar surface of the wafer during the one or more metrology measurements in accordance with the azimuth angle sensitive motion algorithm:
moving the wafer rotationally about a pivot substantially perpendicular to a planar surface of the wafer in accordance with the azimuth angle sensitive motion algorithm:
maintaining at least a part of the set of optics stationary; and
counter balancing the stage, with at least one counter mass, at least one of radial or rotational movement.

25. The method of claim 24, further comprising:
rotating a radial axis of the stage while maintaining the at least a part of the set of optics stationary.

26. The method of claim 24, further comprising:
rotating a part of the optics receiving collimated illumination from one or more stationary optics about an optical axis of the collimated illumination.

27. The method of claim 26, further comprising:
delivering power to a rotatable part of the set of optics;
delivering control instructions to a rotatable part of the set of optics; and
wirelessly receiving data from the rotatable part of the set of optics.

28. The method of claim 24, further comprising:
moving the wafer horizontally; and
moving the set of optics vertically to the wafer.

29. The method of claim 24, further comprising:
moving the wafer vertically; and
moving the set of optics horizontally to the wafer.

30. The method of claim 24, further comprising:
leveling the stage to eliminate a coarse stroke requirement vertically to the stage.

31. An apparatus comprising:
a memory configured to store a set of computer-readable instructions;
a processor configured to execute the set of computer-readable instructions to control movement of a wafer, wherein the processor performs at least an azimuth angle sensitive motion algorithm to determine movement of an R-Theta stage to control movement of a wafer, wherein the movement controlled by the processor includes rotationally actuating the wafer about a pivot substantially perpendicular to a planar surface of the wafer and radially actuating the wafer in a direction substantially parallel to the planar surface of the wafer, wherein at least a part of a set of optics are maintained stationary; and
wherein the processor is configured to execute the set of computer-readable instructions to control movement of at least one counter mass to balance at least one of radial or rotational movement.

32. The apparatus of claim 31, wherein the processor is configured to execute the set of computer-readable instructions to control rotation of a part of the set of optics receiving collimated illumination from a stationary part of the set of optics about an optical axis of the collimated illumination.

33. The apparatus of claim 32, wherein the processor is configured to execute the set of computer-readable instructions to control at least one of power delivery to a rotatable part of the set of optics or data retrieval from the rotable part of the set of optics.

34. The apparatus of claim 31, wherein the processor is configured to execute the set of computer-readable instructions to control horizontal wafer movement and vertical movement of the set of optics.

35. The apparatus of claim 31, wherein the processor is configured to execute the set of computer-readable instructions to control vertical wafer movement and horizontal movement of the set of optics.

36. A metrology tool comprising:
an R-Theta stage comprising:
a pivoted connection arranged to receive a wafer and enable rotation of the wafer about a pivot substantially perpendicular to a planar surface of the wafer;
a radial axis arranged to move radially in a direction substantially parallel to the planar surface of the wafer, the rotatable pivot connection attached thereto; and
a set of optics including a stationary part and a rotatable part, wherein the stationary part is configured to generate a collimated illumination beam and the rotatable part is configured to receive the collimated illumination beam from the stationary part, wherein the stationary part and the rotatable part are mechanically decoupled via a gap, wherein the rotatable part is positioned proximate to the wafer surface;

a controller comprising:
a memory configured to store a set of computer-readable instructions;
a processor configured to execute the set of computer-readable instructions to control movement of a wafer, wherein the movement controlled by the processor includes rotationally actuating the wafer about a pivot substantially perpendicular to a surface of the wafer and radially actuating the wafer in a direction substantially parallel to the surface of the wafer, wherein the processor performs at least an azimuth angle sensitive motion algorithm to control movement of the wafer, wherein at least a part of a set of optics are maintained stationary; and
wherein the processor is configured to execute the set of computer-readable instructions to control movement of at least one counter mass to balance at least one of radial or rotational movement.

37. A metrology tool comprising:
an metrology tool R-Theta stage comprising:
a vertical wafer stage, wherein a line orthogonal to a receiving surface of the vertical wafer stage is substantially horizontal relative to the metrology tool; and
a set of optics arranged perpendicular to the vertical wafer stage; and
a controller comprising:
a memory configured to store a set of computer-readable instructions;
a processor configured to execute the set of computer-readable instructions to control movement of a wafer, wherein the movement controlled by the processor includes rotationally actuating the wafer about a pivot substantially perpendicular to a surface of the wafer and radially actuating the wafer in a direction substantially parallel to the surface of the wafer, wherein the processor performs at least an azimuth angle sensitive motion algorithm to determine movement of the R-Theta stage to control movement of the wafer, wherein at least a part of a set of optics are maintained stationary; and
wherein the processor is configured to execute the set of computer-readable instructions to control movement of at least one counter mass to balance at least one of radial or rotational movement.

* * * * *